US008227515B2

(12) United States Patent
Leoni et al.

(10) Patent No.: US 8,227,515 B2
(45) Date of Patent: Jul. 24, 2012

(54) USE OF HYDROXAMIC ACID DERIVATIVES FOR THE PREPARATION OF ANTI-TUMOUR MEDICAMENTS

(75) Inventors: Flavio Leoni, Milan (IT); Paolo Mascagni, Villasanta (IT)

(73) Assignee: Italfarmaco S.p.A., Milan (IT)

( * ) Notice: Subject to any disclaimer, the term of this patent is extended or adjusted under 35 U.S.C. 154(b) by 865 days.

(21) Appl. No.: 10/542,244

(22) PCT Filed: Dec. 10, 2003

(86) PCT No.: PCT/EP03/14171
§ 371 (c)(1),
(2), (4) Date: Jul. 15, 2005

(87) PCT Pub. No.: WO2004/064824
PCT Pub. Date: Aug. 5, 2004

(65) Prior Publication Data
US 2006/0063800 A1 Mar. 23, 2006

(30) Foreign Application Priority Data

Jan. 17, 2003 (IT) .............................. MI2003A0064

(51) Int. Cl.
*A61K 31/165* (2006.01)
*A61K 31/16* (2006.01)
*A61K 31/325* (2006.01)
*A61P 35/00* (2006.01)
(52) U.S. Cl. .......................... 514/575; 514/576; 514/577
(58) Field of Classification Search .................. None
See application file for complete search history.

(56) References Cited

U.S. PATENT DOCUMENTS 6,034,096 A * 3/2000 Bertolini et al. .............. 514/307

FOREIGN PATENT DOCUMENTS

| EP | 0 901 465 B1 | 3/1999 |
| WO | WO 01/38322 A1 | 5/2001 |
| WO | WO 02/074298 A1 | 9/2002 |
| WO | WO 02/080892 * | 10/2002 |
| WO | WO 03/013493 A1 | 2/2003 |
| WO | WO 03/070691 A1 | 8/2003 |

OTHER PUBLICATIONS

Cecil Textbook of Medicine, 21st edition, 2000, W.B. Saunders, Chapter 198, pp. 1060-1074.*
Johnson et al., British Journal of Cancer, 2001, vol. 48, No. 10, pp. 1424-1431.*
Marks et al., "Histone Deacetylase Inhibitors: Inducers of Differentiation of Apoptosis of Transformed Cells," 2000, Journal of National Cancer Institute, vol. 92, No. 15, pp. 1210-1216.*
The Cecil reference (.Cecil Textbook of Medicine, 21st Edition (2000), Goldman & Bennett (Editors), W.B. Saunders Company (Publisher), Chapter 198, pp. 1060-1074).*
In addition, Johnson et al. (.British Journal of Cancer, 2001, vol. 48, No. 10, pp. 1424-1431).*
Marks et al. (Histone Deacetylase Inhibitors: Inducers of Differentiation of Apoptosis of Transformed Cells, 2000.*
Uesato et al. ("Novel Histone Deacetylase Inhibitors: N-Hydroxycarboxamides Possessing a Terminal Bicyclic Aryl Group," 2002, Bioorganic and Medicinal Chemistry Letters, vol. 12, pp. 1137-1349.*
Bertolini et al. (European Patent Application EP 0 901 465.*
Suganuma, M. et al. Essential role of tumor necrosis factor a (TNF-a) in tumor promotion as revealed by TNF-a-deficient mice. Cancer Res. 59, 4516-4518 (1999).*
Balkwill et al. Inflammation and cancer: back to Virchow? Lancet 2001; 357: 539-545.*
Cubillos et al. Effect of blocking TNF on IL-6 levels and metastasis in a B16-BL6 melanoma/mouse model. Anti-cancer Research 17: 2207-2212 (1997).*
Family list 27 family members for: EP0901465, derived from 21 applications (2 pgs).
EP 0 901 465; (WO 97/43251) Nov. 20, 1997; 43 pgs.
Uesato, S., et al; "Novel Histone Deacetylase Inhibitors: N-Hydroxycarboxamides Possessing a Terminal Bicyclic Aryl Group"; *Bioorganic & Medicinal Chemistry Letters*; vol. 12, pp. 1347-1349 (2002) XP-002276408.
Jung, M., et al; "Amide Analogues of Trichostatin A as Inhibitors of Histone Deacetylase and Inducers of Terminal Cell Differentiation"; *J. Med. Chem.*; vol. 42; pp. 1669-4679 (1999) XP-002144226.
Chemical Abstracts Service; Naka, M., et al; "Preparation of N-acylaminoalkanehydroxamic acids as IL-6 production inhibitors"; Database accession No. 137:247516; XP-002276409 (Abstract).
Nicolaus, B.J.R.; "Symbiotic Approach to Drug Design"; *Decision Making in Drug Research*; pp. 173-186 (1983) XP-002197412.
Chemical Abstracts Service; Uesato, S., et al; "Preparation of N-hydroxycarboxamide derivatives as anticancer agents"; Database accession No. 139:214215; XP002276410 (Abtract).
Bopp, S.K., et al; "Comparison of four different colorimetric and fluorometric cytotoxicity assays in a zebrafish liver cell line"; *BMC Pharmacology*; vol. 8, No. 8; pp. 1-11 (2008).
Marks, P.A., et al; "Histone Deacetylases and Cancer: Causes and Therapies"; *Reviews*; 9 pgs.
Qiu, L., et al; "Anti-tumour activity in vitro and in vivo of selective differentiating agents containing hydroxamate"; *British Journal of Cancer*, vol. 80, No. 8; pp. 1252-1258 (1999).

(Continued)

*Primary Examiner* — David J Blanchard
*Assistant Examiner* — Peter Anthopolos
(74) *Attorney, Agent, or Firm* — Nixon & Vanderhye

(57) ABSTRACT

Method of treating a tumor in a patient in need thereof by administering to the patient an effective amount of 4-[6-(diethylaminomethyl)naphth-2-ylmethyloxycarbamoyl]benzohydrozamic acid.

4 Claims, 1 Drawing Sheet

OTHER PUBLICATIONS

Eggermont, A.M.M., et al; "Regional Application of TNFα in the Treatment of Cancer: A Preclinical-Clinical Interactive Program"; *Journal of Inflammation*; vol. 47, pp. 104-113 (1996).

Nakamoto, T., et al; "A New Method of Antitumor Therapy with a High Dose of TNF Perfusion for Unreasectable Liver Tumors"; *Anticancer Research*, vol. 20; pp. 4087-4096 (2000).

Scheringa, M., et al; "TNF: A brief review with emphasis on its antitumor activity"; *Biotherapy*, vol. 2, pp. 275-281 (1990).

Branellec, D., et al; "Le TNF: Un Agent Antitumoral Aux Frontieres De L'Immunite Et De L'Inflammation"; *Pathologie Bilogie*, vol. 39, No. 3, pp. 230-239 (1991). (English abstract only).

Brouckaert, P.G.G., et al; "*In Vivo* Anti-Tumour Activity of Recombinant Human and Murine TNF, Alone and in Combination with Murine IFN-γ, on a Syngeneic Murine Melanoma"; *Int. J Cancer*; vol. 38, pp. 763-769 (1986).

Zhao, E., et al; "Effects of TNF Alone or in Combination with Chemotherapeutic Agents on Human Ovarian Cancers in Vitro and in Nude Mice"; *Chinese Medical Journal*, vol. 108, No. 8; pp. 571-575 (1995).

Haranaka, K., et al; "Antitumor Activity of Murine Tumor Necrosis Factor (TNF) Against Transplanted Murine Tumors and Heterotransplanted Human Tumors in Nude Mice"; *Int. J. Cancer*; vol. 34, pp. 236-267 (1984).

Miki, T., et al; "Antitumor Effect of Recombinant Human Tumor Necrosis Factor on Human Testicular Tumors Heterotransplanted I Nude Mice"; *Eur Urol*, vol. 25; pp. 242-247 (1994).

Nosoh, Y., et al; "Antitumor Effects of Recombinant Human Tumor Necrosis Factor against Human Tumor Xenografts Transplanted into Nude Mice"; *Japanese Journal of Surgery*; vol. 17, No. 1, pp. 51-54 (1987).

Sherwood, E.R., et al; "Therapeutic Efficacy of Recombinant Tumor Necrosis Factor α in an Experimental Model of Human Prostatic Carcinoma"; *Journal of Biological Response Modifiers*; vol. 9, No. 1, pp. 44-52 (1990).

Shomura, Y., et al; "Recombinant Human Tumor Necrosis Factor—II. Antitumor Effect on Murine and Human Tumors Transplanted in Mice"; *Int. J. Immonopharmac.*; vol. 8, No. 3, pp. 357-368 (1986).

Guillermo, A., et al; "Acute Leukemia After Infliximab Therapy"; *Letters to the Editor*; p. 2577 (2003).

Beyer, M., et al; "Hepatosplenic T-cell lymphomas and therapy with TNF-α-blocking biologics: a risk for psoriasis patients?"; *JDDG*; vol. 3, pp. 191-194 (2009).

Bongartz, T., et al; "Anti-TNF Antibody Therapy in Rheumatoid Arthritis and the Risk of Serious Infections and Malignancies"; *JAMA*; vol. 295, No. 19, pp. 2275-2482 (2006).

Brown, S.L., et al; "Tumor Necrosis Factor Antagonist Therapy and Lymphoma Development"; *Arthritis & Rheumatism*; vol. 46, No. 12, pp. 3151-3158 (2002).

Burger, D.C., et al; "Hepatosplenic T-cell lymphoma following infliximab therapy for Crohn's disease"; *MJA*, vol. 190, No. 6; pp. 341-342 (2009).

Chen, S.C., et al; "Hepatocellular Carcinoma Occurring in a Patient with Crohn's Disease Treated with Both Azathioprine and Infliximab"; *Dig. Dis. Sci.*; vol. 51, pp. 952-955 (2006).

Provenzano, G., et al; "Efficacy of infliximab in psoriatic arthritis resistant to treatment with disease modifying antirheumatic drugs: an open pilot study"; *Ann. Rheum. Dis.*, vol. 62; pp. 680-681 (2003).

Cron, R.Q., et al; "Guilt by association—what is the true risk of malignancy in children treated with etanercept for JIA?"; *Pediatric Rheumatology*, vol. 8, No. 23; pp. 1-3 (2010).

Dahhan, T., et al; "Extra-intestinal Hodgkin's lymphoma in a Crohn's disease patient on long-term azathioprine and infliximab therapy"; *Tropical Gastroenterology*; vol. 31, No. 1, pp. 51-53 (2010).

Dauendorffer, J.N., et al; "Sezary syndrome in a patient receiving infliximab for ankylosing spondylitis"; *British Journal of Dermatology*; vol. 156, pp. 742-743 (2007).

Deneau, M., et al; "Natural Killer Cell Lymphoma in a Pediatric Patient with Inflammatory Bowel Disease"; *Pediatrics*; http://pediatrics.aappublications.org/content/126/4/e977.full.html; vol. 126, pp. e977-e981 (2010).

Diak, P., et al; "Tumor Necrosis Factor α Blockers and Malignancy in Children"; *Arthritis & Rheumatism*; vol. 62, No. 8; pp. 2517-2524 (2010).

Drini, M., et al; "Hepatosplenic T-cell lymphoma following infliximab therapy for Crohn's Disease"; *MJA*, vol. 189, No. 8, pp. 464-465 (2008).

Girard, C., et al; "Gastric MALT lymphoma in a patient receiving infliximab for psoriasis"; *British Journal of Dermatology*, vol. 159, pp. 479-511 (2008).

Grunhagen, D.J., et al; "Isolated Limb perfusion with TNF-α and Melphalan in Locally Advanced Soft Tissue Sarcomas of the Extremities"; *Cancer Research*, vol. 179, pp. 257-270 (2009).

Horneff, G.; "Malignome und Tumor-Nekrose-Faktor-Inhibitroen bei der juvenilen idiopathischen Arthritis"; *Z. Rheumatol*; vol. 69, pp. 516-526 (2010).

Keystone, E.C.; "Does Anti-Tumor Nerosis Factor-α Therapy Affect Risk of Serious Infection and Cancer in Patients with Rheumatoid Arthritis?: A Review of Longterm Data"; *The Journal of Rheumatology*, vol. 38, No. 8, pp. 1-11 (2011).

Kotlyar, D.S., et al; "A Systematic Review of Factors that Contribute to Hepatosplenic T-Cell Lymphoma in Patients with Inflammatory Bowel Disease"; *Clinical Gastroenterology and Hepatology*; vol. 9, pp. 36-41 (2011).

Krelin, Y., et al; "Interleukin-1β-Driven Inflammation Promotes the Development and Invasiveness of Chemical Carcinogen—Induced Tumors"; *Cancer Res.*, vol. 67; pp. 1062-1071 (2007).

Lourari, S., et al; "Cutaneous T-cell lymphoma following treatment of rheumatoid arthritis with tumor necrosis factor-α blocking agents: two cases"; *JEADV*, vol. 23, pp. 954-982 (2009).

Mackey, A.C., et al; "Hepatosplenic T Cell Lymphoma Associated with Infliximab Use in Young Patients Treated for Inflammatory Bowel Disease"; *Journal of Pediatric Gastroenterology and Nutrition*; vol. 44, pp. 265-267 (2007).

Mariette, X., et al; "Lymphoma in patients treated with anti-TNF: results of the 3-year prospective French RATIO registry"; *Ann. Rheum. Dis.*; vol. 69, No. 2, pp. 400-408 (2010).

Melichar, B., et al; "Anorectal Carcinoma After Infliximab Therapy in Crohn's Disease: Report of a Case"; *Disease of the Colon & Rectum*, vol. 49, pp. 1228-1233 (2006).

Nakashima, C., et al; "Diffuse large B-cell lymphoma in a patient with rheumatoid arthritis treated with infliximab and methotrexate"; *Clinical and Experimental Dermatology*, vol. 33, pp. 437-439 (2008).

Ochenrider, M.G., et al; "Hepatosplenic T-Cell Lymphoma in a Young Man With Crohn's Disease: Case Report and Literature Review"; *Clinical Lymphoma, Myeloma & Leukemia*, pp. 144-148 (2010).

Outlaw, W., et al; "Lymphomatoid Papulosis in a Patient with Crohn's Disease Treated with Infliximab"; *Inflamm Bowel Disease*, vol. 15, No. 7, pp. 965-966 (2009).

Pozadzides, J.V., et al; "Hepatosplenic T-cell lymphoma and TNF-α inhibitors"; *Expert Rev. Hematol.*, vol. 2, No. 6, pp. 611-614 (2009).

Rennard, S.I., et al; "The Safety and Efficacy of Infliximab in Moderate to Severe Chronic Obstructive Pulmonary Disease"; *American Journal of Respiratory and Critical Care Medicine*, vol. 175, pp. 926-934 (2007).

Roddy, E., et al; "Non-Hodgkin's lymphoma in a patient with refractory dermatomyositis which had been treated with infliximab"; *Rheumatology*, vol. 41, pp. 1194-1214 (2002).

Rosh, J.R., et al; "Hepatosplenic T-cell Lymphoma in Adolescents and Young Adults with Crohn's Disease: A Cautionary Tale?"; *Inflamm. Bowel Disease*, vol. 13, No. 8, pp. 1024-1030 (2007).

Ruperto, N., et al; "JIA, treatment and possible risk of malignancies"; *Nature Reviews/Rheumatology*, vol. 7, pp. 6-7 (2011).

Suganuma, M., et al; "TNF-α-inducing protein, a carcinogenic factor secreted from *H. pylori*, enters gastric cancer cells"; *Int. J. Cancer*, vol. 123, pp. 117-122 (2008).

Suganuma, M., et al; "Discrete roles of cytokines, TNF-α, IL-1, IL-6 in tumor promotion and cell transformation"; *International Journal of Oncology*; vol. 20, pp. 131-136 (2002).

Suganuma, M., et al; "Carcinogenic Role of Tumor Necrosis Factor-α Inducing Protein of *Helicobactor pylori* in Human Stomach"; *Journal of Biochemistry and Molecular Biology*, vol. 39, No. 1, pp. 1-8 (2006).

Suganuma, M., et al; "New tumor necrosis factor-α-inducing protein released from *Helicobactor pylori* for gastric cancer progression"; *J. Cancer. Res. Clin. Oncol.*, vol. 131, pp. 305-313 (2005).

Veeraputhiran, M., et al; "Sudden loss of the GVL effect following use of the TNF inhibitor infliximab in a chronic myelogenous leukemia patient with chronic GVHD"; *Bone Marrow Transplantation*, vol. 45, pp. 1113-1114 (2010).

Veres, G., et al; "Infliximab therapy for pediatric Crohn's disease"; *Expert Opin. Biol. Ther.*, vol. 7, No. 12, pp. 1869-1880 (2007).

Wolfe, F., et al; "Lymphoma in Rheumatoid Arthritis"; *Arthritis & Rheumatism*, vol. 50, No. 6, pp. 1740-1751 (2004).

Yildirim-Toruner, C, et al; "Hodgkin's Lymphoma and Tumor Necrosis Factor Inhibitors in Juvenile Idiopathic Arthritis"; *The Journal of Rheumatology*, vol. 35, No. 8, pp. 1679-1688 (2008).

Alcain, G., et al; "Acute Leukemia for Infliximab Therapy"; *Letters to the Editor.*, vol. 98, p. 2577 (2003).

Bonvalot, S., et al; "La perfusion pelvienne sous circulation extracorporelle dans les tumerus pelviennes localement évoluées"; *Bulletin du Cancer*; vol. 96, No. 1; pp. 103-109 (2009).

Bonvalot, S., et al; "Hyperthermic Isolated Limb Perfusion in Locally Advanced Soft Tissue Sarcoma and Progressive Desmoid-Type Fibromatosis with TNF 1 mg and Melphalan (T1-M HILP) is Safe and Efficient"; *Ann. Surg. Oncol.*, vol. 16, pp. 3350-3357 (2009).

Cherix, S., et al; "Isolated Limb Perfusion with Tumor Necrosis Factor and Melphalan for Non-Resectable Soft Tissue Sarcomas: Long-Term Results on Efficacy and Limb Salvage in a Selected Group of Patients"; *Journal of Surgical Oncology*, vol. 98, pp. 148-155 (2008).

Cohen, C.D., et al; "Kaposi's sarcoma associated with tumour necrosis factor α neutralising therapy"; *Ann. Rheum. Dis.*, vol. 62, p. 684 (2003).

Deroose, J.P., et al; "Isolated limb perfusion for melanoma in-transit metastases: developments in recent years and the role of tumor necrosis factor alpha"; *Curr. Opin. Oncol.*; vol. 23, pp. 183-188 (2011).

Drouet, A., et al; "Common peroneal nerve palsy following TNF-based isolated limb perfusion for irresectable extremity desmoids tumor"; *Orthopaedics & Traumatology: Surgery & Research*, vol. 95, pp. 639-644 (2009).

Duprat, J.P., et al; "Long-term response of isolated limb perfusion with hyperthermia and chemotherapy for Merkel cell carcinoma"; *Eur. J. Surg. Oncol.*; vol. 35, pp. 568-572 (2009).

Gerspach, J.K., et al; "Improving TNF as a cancer therapeutic: Tailor-made TNF fusion proteins with conserved antitumor activity and reduced systemic side effects"; *Int 'l Union of Biochemistry and Molecular Biology, Inc.*, vol. 35, pp. 364-372 (2009).

Grabellus, F., et al; "Evaluation of 47 Soft Tissue Sarcoma Resection Specimens after Isolated Limb Perfusion with TNF-α and Melphalan: Histologically Characterized Improved Margins Correlate with Absence of Recurrences"; *Ann. Surg. Oncol.*, vol. 16, pp. 676-686 (2009).

Moreno-Ramirez, D., et al; "Isolated Lamb Perfusion for Malignant Melanoma: Systemic Review on Effectiveness and Safety"; *The Oncologist*, vol. 15, pp. 416-427 (2010).

Nachmany, I., et al; "Efficacy of high vs low dose TNF-isolated limb perfusion for locally advanced soft tissue sarcoma"; *Eur. J. Surg. Oncol.*, vol. 35, pp. 209-214 (2009).

Rossi, C.R., et al; "Long-Term Results of Melphalan-Based Isolated Lamb Perfusion with or without Low-Dose TNF for In-Transit Melanoma Metastases"; *Ann. Surg. Oncol.*, vol. 17, pp. 3000-3007 (2010).

Bots, M., et al; "Rational Combinations Using HDAC Inhibitors"; *Clinical Cancer Research*, vol. 15, pp. 3970-3977 (2009).

Chou, T.C.; "Drug Combination Studies and Their Synergy Quantification Using the Chou-Talalay Method"; *Cancer Research*, vol. 70, pp. 440-446 (2010).

Chou, T.C.; "Theoretical Basis, Experimental Design, and Computerized Simulation of Synergism and Antagonism in Drug Combination Studies($^s$ )"; *Pharmacological Reviews*, vol. 58, No. 3, pp. 621-681 & p. 124 (2006).

Chou, T.C., et al; "Quantitative Analysis of Dose-Effect Relationships: The Combined Effects of Multiple Drugs or Enzyme Inhibitors"; *Advanced Enzyme Regul.*, pp. 27-55 (1984).

Italfarmaco, ITF2357, "Chemical Diethyl-[6-(4-hydroxycarbamoyl-phenylcarbamoyloxymethyl)-naphthalen-2-ylmethyl]-ammonium chloride monohydrate" *Investigator's Brochure*; 2 pgs (Jan. 2012).

Italfarmaco S.p.A., ITF2357 *Investigator's Brochure*; pp. 84, 85, 86 (Jan. 2012).

Leoni, F., et al; "The Histone Deacetylase Inhibitor ITF2357 Reduces Production of Pro-Inflammatory Cytokines in Vitro and Systemic Inflammation in Vivo"; *Molecular Medicine*, vol. 11, No. 1-12 (2005).

Miller, C.P., et al; "Therapeutic Strategies to Enhance the Anticancer Efficacy of Histone Deacetylase Inhibitors"; *Journal of Biomedicine and Biotechnology*, vol. 2011, Article ID 514261, pp. 1-17 (2011).

Reynolds, C. P., et al; "Evaluating Response to Antineoplastic Drug Combinations in Tissue Culture Models"; *Methods in Molecular Medicine*, vol. 110: *Chemosentisivity*, vol. 1: *In Vitro Assays*, pp. 173-183 (2005).

Thurn, K.T., et al; "Rational therapeutic combinations with histone deacetylase inhibitors for the treatment of cancer"; *Future Oncol.*, vol. 7, No. 2, pp. 263-283 (2011).

\* cited by examiner

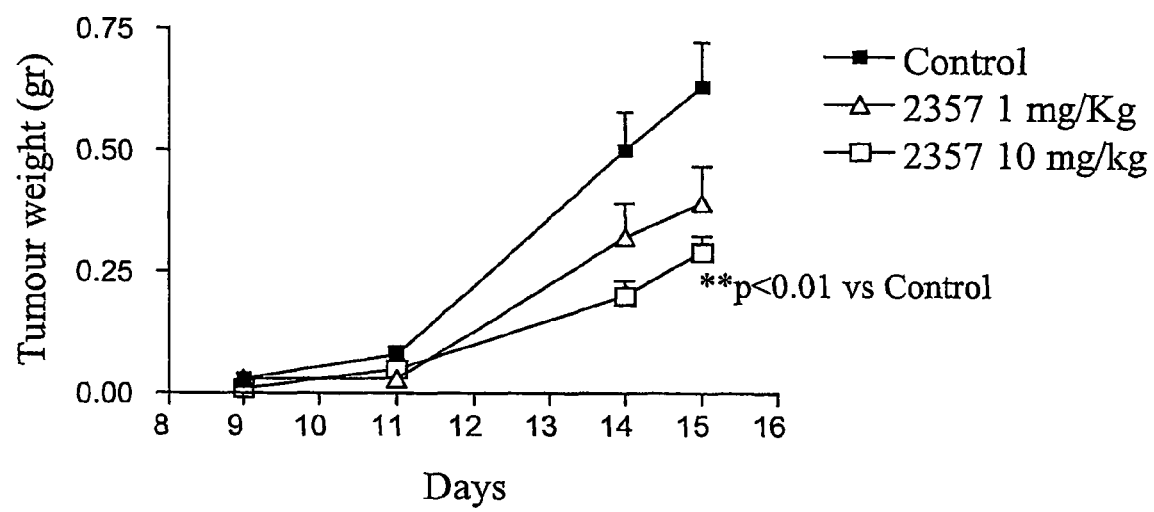

USE OF HYDROXAMIC ACID DERIVATIVES FOR THE PREPARATION OF ANTI-TUMOUR MEDICAMENTS

This application is the U.S. National Phase of International Application PCT/EP2003/014171, filed 10 Dec. 2003, which designated the U.S. PCT/EP2003/014171 claims priority to Italian Application No. MI2003A000064 filed 17 Jan. 2003. The entire content of these applications are incorporated herein by reference.

DESCRIPTION

The present invention relates to the use of hydroxamic acid derivatives containing an amidobenzoic moiety for the preparation of anti-tumour medicaments.

BACKGROUND OF THE INVENTION

Hydroxamic acid derivatives containing an amidobenzoic moiety are disclosed in EP 901465 as potential medicaments with anti-inflammatory and immuno-suppressive activity, ascribable to the inhibition of the production of pro-inflammatory cytokines, in particular Tumour Necrosis Factor and interleukin-1-beta.

Said derivatives are represented by the following general formula (I)

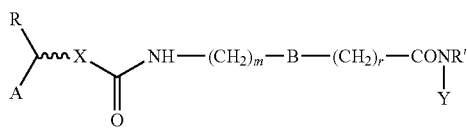

wherein
R' is hydrogen or $(C_{1-4})$alkyl;
A is adamantyl or a mono-, bi- or tricyclic residue, which can optionally be partially or completely unsaturated, contain one or more heteroatoms selected from the group consisting of N, S or O, and optionally substituted with hydroxy, alkanoyloxy, primary, secondary or tertiary amino, amino$(C_{1-4})$alkyl, mono- or di-$(C_{1-4})$alkyl-amino$(C_{1-4})$alkyl, halogen, $(C_{1-4})$alkyl, tri$(C_{1-4})$alkylammonium-$(C_{1-4})$alkyl;
∼∼∼is a 1 to 5 carbon atoms chain optionally containing a double bond or a NR' group wherein R' is as defined above;
R is hydrogen or phenyl;
X is an oxygen atom or a NR' group wherein R' is either as defined above or absent;
r and m are independently 0, 1 or 2;
B is a phenylene or a cyclohexylene ring;
Y is hydroxy or an amino$(C_{1-5})$alkyl chain optionally interrupted by an oxygen atom;
with the proviso that a tricyclic group as defined for A is fluorenyl only when, at the same time, X is different from Ol and Y is different from hydroxy, unless said fluorenyl is substituted with a tri$(C_{1-4})$alkylammonium$(C_{1-4})$alkyl group.

Preferred compounds of formula (I) are those in which R' is hydrogen, A is optionally substituted phenyl or 1- or 2-naphthyl, cyclohexyl, 1- or 2-1,2,3,4-tetrahydronaphthyl, adamantyl, quinolinyl, isoquinolinyl, 1- or 2-indenyl, tetrahydroquinolinyl, tetrahydroisoquinolinyl.

Most preferred are the compounds (I) in which A is phenyl or 1- or 2-naphthyl, R is phenyl when A is phenyl or is hydrogen when A is 1- or 2-naphthyl.

Said compounds can be prepared according to methods disclosed in EP 901465, herein incorporated by reference.

SUMMARY OF THE INVENTION

It has now been found that the compounds of formula (I) are endowed with anti-tumour activity both in vitro and in vivo.

The invention relates therefore to the use of compounds of formula (I)

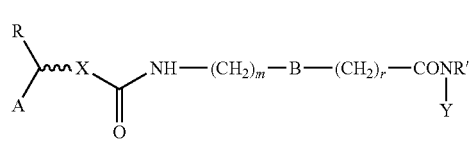

wherein
R' is hydrogen or $(C_{1-4})$alkyl;
A is adamantyl or a mono-, bi- or tricyclic residue, which can optionally be partially or completely unsaturated, optionally containing one or more heteroatoms selected from the group consisting of N, S or O, and optionally substituted substituted with hydroxy, alkanoyloxy, primary, secondary or tertiary amino, amino$(C_{1-4})$alkyl, mono- or di-$(C_{1-4})$alkyl-amino$(C_{1-4})$alkyl, halogen, $(C_{1-4})$alkyl, tri$(C_{1-4})$alkylammonium-$(C_{1-4})$alkyl;
∼∼∼is a 1 to 5 carbon atoms chain optionally containing a double bond or a NR' group wherein R' is as defined above;
R is hydrogen or phenyl;
X is an oxygen atom or a NR' group wherein R' is either as defined above or absent;
r and m are independently 0, 1 or 2;
B is a phenylene or a cyclohexylene ring;
Y is hydroxy or an amino$(C_{1-5})$alkyl chain optionally interrupted by an oxygen atom;
with the proviso that a tricyclic group as defined for A is fluorenyl only when, at the same time, X is different from O and Y is different from hydroxy, unless said fluorenyl is substituted with a tri$(C_{1-4})$alkylammonium$(C_{1-4})$alkyl group for the preparation of anti-tumor medicaments.

Compounds (I) can be used for the treatment of neoplasias of different origin, in particular of melanomas, colon, lung and breast carcinomas, neuroblastomas, sarcomas, various forms of leukaemia (erythroleukaemia, acute promyelocytic leukaemia) and the like, at daily single or multiple doses ranging from 1 to 500 mg, depending on the disease and pharmaceutical and toxicological characteristics of the considered compound, which can be administered as suitable formulations through the oral, parenteral or topical route, for example through direct perfusion at the site of the tumour lesion. Moreover, the compounds of formula (I) can be administered in combination with other known antineoplastic agents, according to polychemotherapy protocols.

The activity of the compounds of formula (I) was evidenced in vitro, on cultured tumour cell lines, and in vivo, on the experimental model of the murine melanoma B16-BL6.

BRIEF DESCRIPTION OF THE DRAWINGS

The invention will be further described with reference to the accompanying FIGURE which shows plots of tumor weights versus Days.

EXAMPLES

The following examples illustrate the invention in greater detail.

Example 1

In Vitro Activity

The anti-tumour effect of the compound of example 12 of EP 901465, 4-[6-(diethylaminomethyl)naphth-2-ylmethyloxycarbamoyl)] benzohydroxamic acid hydrochloride (ITF 2357), was tested in vitro by measuring the capacity of the compound to inhibit the growth of tumour cell lines of different histotype deriving from both solid tumours and haematological tumours. The cell lines used were: A549 (pulmonary carcinoma), MDA-MB435 (breast carcinoma) and KG-1 (myeloid leukaemia).

A549 and MDA-MB435 cells (respectively grown in E-MEM and D-MEM culture medium, supplemented with 10% of fetal calf serum) were seeded on 96 wells-flat bottom-plates (5000 cells/well) and allowed to adhere for 4 hours at 37° C. under 5% $CO_2$ atmosphere. Thereafter ITF 2357 at various doses was added to each well (4 replicates). After further 36 hours, tritiated thymidine (1 µCi/well) was added to each well and left therein for the following 12 hours. After this time, the cells were washed 3 times with culture medium and then solubilized with 1N NaOH for 30 minutes.

A liquid scintillation beta counter was used for measurement of the radioactivity contained in each sample, which is directly proportional to DNA synthesis and therefore to cell proliferation. KG-1 cells, grown in RPMI 1640 culture medium, supplemented with 5% fetal calf serum, were seeded in 96 wells-flat bottom-plates (250000 cells/well). ITF 2357 at various doses was immediately added and after 36 hours tritiated thymidine was added to each well (1 µCi/well) and left therein for the following 12 hours. At the end the cells were collected by a cell harvester and the radioactivity contained in each sample which is directly proportionated to DNA synthesis and therefore to cell proliferation was measured by a liquid scintillation beta counter.

The effect of different doses of ITF 2357 was measured as percent of inhibition of radioactivity incorporation compared with untreated control cells. The concentration capable of inducing a 50% cell growth inhibition ($IC_{50}$) was then determined by means of linear regression.

The results obtained are summarized in the following table:

|            | Cell line |          |       |
|------------|-----------|----------|-------|
|            | A549      | MDA-MB435 | KG-1  |
| $IC_{50}$(nM) | 495       | 73       | 552   |

The results obtained show that ITF 2357 inhibits in vitro, at very low dosages (range 10-9M), the growth of the cell lines employed. ITF 2357 in particular inhibits cell growth both of cells from solid tumours (A549 and MDA-MB435) and from leukaemias (KG-1), therefore suggesting its use on tumours of different histotype.

Example 2

In Vitro Activity

Cell lines derived from human solid tumours of different histotype and stabilised in vitro were used in the following experiment. In particular, three cell lines from head and neck tumours (KB, Ca127 and Hep2), two cell lines derived from colon carcinomas (HT-29 and LoVo) and four cell lines derived from melanomas (Colo38, Pes41, Pes43 and Anad) were studied.

The cells were grown according to conventional methods in flasks containing synthetic culture medium added with fetal serum, at 37° C. under 5% $CO_2$ atmosphere, then seeded in 96 wells plates and allowed to adhere for some hours. ITF 2357 was added in triplicate at increasing doses to each well and the cells were incubated for further 72 hours. Viable cells were labelled by dyeing with sulforhodamine B and their amount was determined by spectrophotometric evaluation of the dye content in each well. The effect of ITF 2357 was calculated as percentage of inhibition, at each concentration, of the dye incorporation in wells containing ITF 2357 compared with control wells (cells without drug). $IC_{50}$ values of ITF 2357 were calculated by Software Calcusyn (Biosoft) according to dose-response curves.

| Cell line | Tumour origin   | ITF 2357 $IC_{50}$ (µM) |
|-----------|-----------------|-------------------------|
| KB        | Head-neck       | 0.64                    |
| Cal27     | Head-neck       | 3.4                     |
| Hep-2     | Head-neck       | 1                       |
| HT-29     | Colon carcinoma | 0.7                     |
| LoVo      | Colon carcinoma | 2.5                     |
| Colo38    | Melanoma        | 2.38                    |
| Pes41     | Melanoma        | 1.6                     |
| Pes43     | Melanoma        | 1.4                     |
| Anad      | Melanoma        | 5.7                     |

Example 3

In Vivo Activity

The anti-tumour effect of ITF 2357 was studied measuring the capacity of the compound to reduce the growth of the murine melanoma B16-BL6.

B16-BL6 tumour is a highly metastatic variant (Sciumbata T. et al. Invasion and Metastasis 1996; 16: 132-143) of the native tumour B16 and it grows subcutaneously in the syngenic mouse C57BL/6 (Gutman M et al. Cancer Biother. 1994; 9(2): 163-170).

B16-BL6 tumour cells were inoculated subcutaneously in female C57BL/6 mice (10 animals/group, weight 20-22 grams) at the dose of $2\times10^5$ cells/mouse. ITF 2357 dissolved in water was administered orally, at the indicated doses, 10 minutes before the inoculum of the tumour cells and then daily for 6 days a week. The tumour growth was expressed as tumour weight, measuring twice a week, by means of a calibre, the two perpendicular diameters of the nodules. The weight was calculated according to the formula: (diameter 1×diameter 2)²/2 as described in Giavazzi R. et al. Cancer Res. 1986; 46: 1928-1933.

The results obtained are reported in the enclosed FIGURE.

It can be observed that ITF 2357 exerts a dose-dependent inhibitory effect on the tumour growth, since it reduced of about 50% the volume of the tumoural nodule after 15 days of treatment.

The invention claimed is:

1. Method of treating a solid tumor or hematological tumor in a patient in need of such treatment, the method comprising administering to said patient an effective amount of 4-[6-(diethylaminomethyl)naphth-2-ylmethyloxycarbamoyl]benzohydroxamic acid in combination with an antineoplastic agent, wherein said solid tumor or hematological tumor is selected from the group consisting of melanoma, colon tumor, lung carcinoma, breast carcinoma, sarcoma, and leukaemia.

2. Method according to claim 1, wherein said leukaemia is selected from erythroleukaemia and promyelocytic leukaemia.

3. Method according to claim 1 wherein said 4-[6-(diethylaminomethyl)naphth-2-ylmethyloxycarbamoyl]benzohydroxamic acid is administered in a dosage of 1 to 500 mg.

4. Method according to claim 1 wherein said 4-[6-(diethylaminomethyl)naphth-2-ylmethyloxycarbamoyl]benzohydroxamic acid is administered in single or multiple doses.

* * * * *